United States Patent
Khattar et al.

(10) Patent No.: US 6,348,164 B1
(45) Date of Patent: Feb. 19, 2002

(54) PROCESS FOR IMPROVING SHELF STABILITY OF LIQUID OVERBASED CALCIUM CARBOXYLATES, MIXED METAL STABILIZERS CONTAINING SAME, AND STABILIZING HALOGEN-CONTAINING POLYMERS THEREWITH

(75) Inventors: Rajesh Khattar, Richmond Heights; Benjamin Paul Labovitz, Cleveland Heights; Paulette Baker, Chagrin Falls, all of OH (US)

(73) Assignee: OMG Americas, Inc., Cleveland, OH (US)

( * ) Notice: Subject to any disclaimer, the term of this patent is extended or adjusted under 35 U.S.C. 154(b) by 0 days.

(21) Appl. No.: 09/309,456

(22) Filed: May 11, 1999

Related U.S. Application Data

(62) Division of application No. 08/918,488, filed on Aug. 26, 1997, now abandoned.

(51) Int. Cl.[7] .................. C09K 19/02; C09K 19/04; C09K 19/08; C08K 11/00
(52) U.S. Cl. ............ 252/404; 252/400.24; 252/400.52; 252/400.53; 252/400.62; 524/327; 524/368; 524/377; 524/436; 524/450
(58) Field of Search .................. 252/400.62, 400.24, 252/404, 400.52, 400.53; 524/357, 400, 327, 368, 377, 436, 450

(56) References Cited

U.S. PATENT DOCUMENTS

| | | | |
|---|---|---|---|
| 2,616,904 A | 11/1952 | Asseff et al. | 260/399 |
| 2,760,970 A | 10/1956 | Le Suer | 260/139 |
| 2,767,164 A | 10/1956 | Asseff et al. | 260/139 |
| 2,798,852 A | 7/1957 | Wiese et al. | 252/42.7 |
| 2,802,816 A | 8/1957 | Asseff et al. | 260/139 |
| 3,027,325 A | 3/1962 | McMillen et al. | 252/33 |
| 3,031,284 A | 4/1962 | Andress, Jr. et al. | 44/76 |
| 3,194,823 A | 7/1965 | Le. Suer et al. | 260/414 |
| 3,342,733 A | 9/1967 | Robbins et al. | 252/33 |
| 3,533,975 A | 10/1970 | Scullin | 260/23 |
| 3,764,571 A | 10/1973 | Jennings et al. | 260/23 XA |
| 3,773,664 A | 11/1973 | Lesuer | 252/40.7 |
| 3,779,922 A | 12/1973 | LeSuer | 252/34.7 |
| 4,159,973 A | 7/1979 | Hoch et al. | 260/23 XA |
| 4,252,698 A | 2/1981 | Ito et al. | 260/18 EP |
| 4,345,045 A | 8/1982 | Jennings et al. | 524/180 |
| 4,655,117 A | 4/1987 | Quinn | 524/327 |
| 4,782,170 A | 11/1988 | Bae et al. | 556/13 |
| 5,004,776 A * | 4/1991 | Tadenuma et al. | 524/377 |
| 5,147,917 A | 9/1992 | Sugawara et al. | 524/357 |
| 5,322,872 A | 6/1994 | Quinn | 524/186 |
| 5,380,832 A | 1/1995 | Benda et al. | 508/460 |
| 5,519,076 A * | 5/1996 | Odaira et al. | 524/112 |
| 5,656,202 A | 8/1997 | Brecker et al. | 252/400.52 |

* cited by examiner

Primary Examiner—Shean C. Wu
(74) Attorney, Agent, or Firm—Wood, Herron & Evans, L.L.P.

(57) ABSTRACT

Shelf stable liquid overbased calcium carboxylates are prepared by reacting a calcium base with a monocarboxylic acid, and carbonating in the presence of a promoter mixture with a phenol and an alcohol under controlled temperature conditions, to produce shelf stable liquids. Mixed metal stabilizer compositions are prepared by blending the stable liquid calcium carboxylate with a metal carboxylate of zinc, cadmium or tin. The mixed metal carboxylates are also shelf stable and are used for stabilizing halogen-containing polymers to provide heat stability, clarity and improved plate out properties.

24 Claims, No Drawings

PROCESS FOR IMPROVING SHELF STABILITY OF LIQUID OVERBASED CALCIUM CARBOXYLATES, MIXED METAL STABILIZERS CONTAINING SAME, AND STABILIZING HALOGEN-CONTAINING POLYMERS THEREWITH

This application is a Division of Ser. No. 08/918,488 filed Aug. 26, 1997,abandoned.

FIELD OF THE INVENTION

The present invention relates to a process for producing shelf stable liquid overbased calcium carboxylates and mixed metal stabilizers containing the overbased calcium carboxylate and a metal carboxylate of zinc, cadmium or tin. The shelf stable mixed metal stabilizer compositions are used as stabilizers for halogen-containing polymers such as polyvinyl chloride (PVC).

BACKGROUND OF THE INVENTION

The preparation of overbased calcium or barium salts of carboxylic acids, alkyl phenols, and sulfonic acids are disclosed in the following U.S. Pat. Nos. 2,616,904; 2,760, 970; 2,767,164; 2,798,852; 2,802,816; 3,027,325; 3,031, 284; 3,342,733; 3,533,975; 3,773,664; and 3,779,922. The use of these overbased metal salts in the halogen-containing organic polymer is described in the following U.S. Pat. Nos. 4,159,973; 4,252,698; and 3,194,823. The use of overbased barium salt in stabilizer formulations has increased during recent years. This is due, in the main, to the fact that overbased barium salts possess performance advantages over the neutral barium salts. The performance advantages associated with overbased barium salts are low plate-out, excellent color hold, good long-term heat stability performance, good compatibility with the stabilizer components, etc. Unfortunately, most of the overbased barium salts are dark in color and, while these dark colored overbased barium salts are effective stabilizers for halogen-containing organic polymer, their dark color results in the discoloration of the end product. This feature essentially prohibits the use of dark colored overbased barium salts in applications where a light colored polymer product is desired.

According to the teachings of U.S. Pat. No. 4,665,117, light colored alkali or alkaline earth metal salts are prepared where alkyl phenol is used as a promoter. However, alkyl phenol is also a major cause for the development of color in the final product. This problem is overcome by the use of propylene oxide which displaces the hydrogen of the phenolic hydroxyl group and thereby restricts the formation of colored species. However, there are disadvantages associated with this approach, principally due to the toxic nature of propylene oxide. Propylene oxide is classified as a possible carcinogen and laboratory animal inhalation studies have shown evidence of a link to cancer. Propylene oxide is also listed as a severe eye irritant, and prolonged exposure to propylene oxide vapors may result in permanent damage to the eye. Furthermore, propylene oxide is extremely flammable and explosive in nature under certain conditions. Propylene oxide boils at 94° F. and flashes at −20° F. As a result, extreme precautions are required to handle propylene oxide at the plant site. Special storage equipment is required for propylene oxide and other safety features are necessary. U.S. Pat. No. 4,665,117 describes the use of propylene oxide at 150° C. At this temperature, propylene oxide will be in the gaseous phase. Under these operating conditions, more than stoichiometric amounts of propylene oxide are required to carry the reaction to completion because propylene oxide will escape from the reaction mixture and this requires additional handling of the excess propylene oxide.

With the movement in the plastics industry to remove heavy metals, liquid calcium-zinc stabilizers are desirous, but not practical, as replacements for barium-cadmium or barium-zinc. Low metal concentrations, poor compatibility, haziness in clear products and plate out during processing in PVC have severely limited the universal acceptance of calcium based liquid stabilizer compositions. Problems are encountered in the stability of these compositions upon standing or storage. Storage stability is due to the incompatibility among the metal salts employed in the composition and is exhibited by increased turbidity, viscosity, or insoluble solids over time. As a result, the liquid calcium compositions are no longer homogeneous or readily pourable and must be specially treated in order to be used. U.S. Pat. No. 5,322,872 is directed to stabilized compositions of mixed metal carboxylates having improved storage stability. According to this patent, a complexing agent is added to the mixed metal carboxylate in order to improve shelf stability. Complexing agents disclosed in this patent include phosphines, phosphites, aromatic cyanides, aromatic hydroxy compounds, oximes and other compounds.

Notwithstanding the state of the art as exemplified by the above patents, there is a need for further improvements in making shelf stable compositions of calcium carboxylates and in methods for their use in stabilizing halogen-containing polymers.

SUMMARY OF THE INVENTION

The present invention relates to a process for making a shelf stable liquid overbased calcium carboxylate and a mixed metal stabilizer composition of (a) an overbased calcium carboxylate/carbonate and (b) a metal carboxylate. The metal carboxylate is preferably selected from the group of zinc, cadmium and tin fatty acid salts. The process involves preparing a reaction mixture containing a basic calcium carboxylate/carbonate under controlled temperature conditions with a mixture of alcohol and phenolic promoters to make a stable liquid. The stable liquid is then added to the metal carboxylate to provide the shelf stable mixed metal stabilizer composition.

The overbased calcium carboxylate/carbonate is made by reacting a basic calcium compound, a carboxylic acid, a phenol/alcohol promoter mixture and carbon dioxide to produce a stable liquid. The temperature conditions of the reaction mixture must be controlled up to a temperature of about 80° C., preferably in the range of about 15° C. to about 80° C., to produce a stable liquid. Above about 80° C., the reaction stalls and the desired stable liquid product is not obtained. Thereafter, the stable liquid is added to a metal soap stabilizer selected from the group of zinc, cadmium and tin carboxylates to provide a shelf stable mixed metal stabilizer composition.

The liquid overbased calcium carboxylate/carbonate may be first treated with an organic phosphite to react with any phenolic color-producing component to improve its color as disclosed in U.S. Pat. No. 5,859,267, and this application in its entirety is incorporated herein by reference. As disclosed in that patent application, organic phosphites suitable for use include various diorganic phosphites and triorganic phosphites to react with color species which may be produced by or in conjunction with the phenol.

A number of benefits are obtained by the inventive process over the prior art methods. Improvements in shelf stability of liquid overbased calcium carboxylates are achieved. Also, shelf stable mixed metal stabilizer systems of an overbased calcium carboxylate/carbonate and metal soap stabilizers are obtained. For example, enhanced shelf stability for the liquid overbased calcium carboxylates and mixed metal stabilizer compositions of this invention have been demonstrated over presently commercially available products. Whereas, in contrast, presently available liquid overbased calcium carboxylates exhibit an early development of turbidity, the liquid compositions of this invention remain stable over extended periods of time. Therefore, they allow easy handling, storage and filtration. When the mixed metal stabilizer systems containing the liquid calcium carboxylates are employed in vinyl halide polymers, they exhibit better compatibilities with improvements in thermal stability, clarity and plate out.

DESCRIPTION OF THE PREFERRED EMBODIMENTS

A. Shelf Stable Liquid Overbased Calcium Carboxylate

Highly overbased calcium carboxylate is prepared by reacting calcium hydroxide with oleic acid in the presence of a mixture of alcohols and alkyl phenol followed by bubbling carbon dioxide through the reaction mixture. The product contains about 13–14% calcium. This product, when combined with other stabilizer additives, for example zinc carboxylate, phosphite, anti-oxidant, β-diketones, etc., produced a shelf stable mixed calcium/zinc stabilizer composition. Up until this invention, making a shelf stable calcium/zinc stabilizer composition was a problem due to the limited solubility of the available 14% calcium carboxylate. For example, PlastiStab 2118, produced by Lubrizol, is a hazy stabilizer composition and the haze eventually settles out thereby disturbing the homogeneity of the stabilizer. However, with the products and mixed metal stabilizers of this invention, shelf stabilities are achieved.

More generally, the process of the present invention for improving the stability of basic calcium carboxylates and mixed metal stabilizers comprises the steps of (A) preparing, in the absence of free oxygen, a mixture comprising a calcium metal base, at least one monocarboxylic acid, and a phenolic/alcohol promoter mixture to facilitate the incorporation of the calcium into the overbased carboxylate, and the ratio of equivalents of the calcium base to the combination of the other components being greater than 1:1, (B) treating said mixture with an acidic gas in the absence of free oxygen until the titratable basicity (phenolphthalein indicator) of the mixture has been substantially reduced, and (C) treating the reaction mixture containing the basic calcium organic salt with an organic phosphite which reacts with the color-producing component present in the final mixture. It is preferred that the entire process involving steps (A), (B) and (C) be conducted in the absence of free oxygen since the presence of oxygen or oxidizing agents results in more highly colored product. Generally, the process is conducted in an atmosphere of nitrogen.

The most critical features of the method include the use of a phenol or alkyl phenol and alcohol as the carbonation aid or promoter. Furthermore, the temperatures of the reaction must be controlled up to about 80° C., preferably in the ranges of about 15° C. to about 80° C. It has been unexpectedly found that stable liquid overbased calcium carboxylates can be produced by this method. Moreover, these liquids are compatible in the mixed metal stabilizer system with a metal carboxylate (a metal carboxylate soap), such as zinc octoate. It is also preferred to include step (C) wherein the basic calcium organic salt, which is produced as an intermediate or reaction product at the conclusion of step (B), is treated with an organic phosphite capable of inhibiting and/or destroying the color-producing component or product which may be generated by the phenol or phenolic reaction product in the above-described reaction. If the color-producing component is not inhibited and/or destroyed in accordance with the method of the above identified '642 application, the product obtained by the process is darker in color and, on standing, continues to darken in color. When the process of that application is followed, the initial product is light in color and does not appreciably darken on standing. Acceptable color by ASTM D1500 standard is up to about 3, preferably about 1 to 2.

B. Overbased Calcium Carboxylates

Throughout this specification and claims, the term "basic" or "overbased" as applied to the calcium organic salts is used to refer to calcium compositions wherein the ratio of total metal contained therein to the organic moieties is greater than the stoichiometric ratio of the neutral metal salt. That is, the number of calcium equivalents is greater than the number of equivalents of the organic moiety. In some instances, the degree to which excess calcium is found in the basic metal salt is described in terms of a "metal ratio". Metal ratio as used herein indicates the ratio of total calcium in the oil-soluble composition to the number of equivalents of the organic moiety. The basic metal salts often have been referred to in the art as "overbased" or superbased" to indicate the presence of an excess of the basic component.

The calcium metal base is utilized in the process and may be derived from any of the alkaline earth metals. The calcium metal bases include the metal oxides and hydroxides, and in some instances, the sulfides, hydrosulfides, etc. In addition to the calcium metal base, the reaction mixture contains at least one monocarboxylic acid. The monocarboxylic acids may be aliphatic or aromatic monocarboxylic acids or mixtures thereof. Among the aliphatic monocarboxylic acids which can be utilized in the present invention are the aliphatic monocarboxylic acids containing an average of at least about 6 carbon atoms and more generally an average of from about 6 to about 30 carbon atoms. The mixture useful in step (A) contains at least one phenol, preferably an alkyl phenol, and an aliphatic alcohol which serve as promoters in the overall process. The alkyl phenols preferably include dodecylphenol and nonylphenol. The alcohols which are useful as promoters include any one of the various available substituted or unsubstituted aliphatic or cycloaliphatic alcohols containing from 1 to about 20 or more carbon atoms. The amounts of the phenol and alcohol included in the mixture as promoters are not critical. The promoters are included in the mixture to contribute to the utilization of the acidic gas during treatment of the mixture with the acidic gas. Generally, at least about 0.1 equivalent and preferably from about 0.05 to about 1.5 equivalents of the phenol and the alcohol per equivalent of a monocarboxylic is employed. Water, which may optionally also be present in the mixture, may be present as water added as such to the mixture, or the water may be present as "wet alcohol", "wet" phenol, hydrates of the alkali or alkaline earth metal salts, or other type of chemically combined water with the metal salts.

In addition to the components described above, the reaction mixtures used to prepare the basic metal salts ordinarily will contain a diluent. Generally, any hydrocarbon diluent can be employed, and the choice of diluent is dependent in part on the intended use of the mixture. Most generally, the hydrocarbon diluent will be a non-volatile diluent such as the various natural and synthetic oils of lubricating viscosity.

The amount of calcium metal base utilized in the preparation of basic carboxylates preferably provides a highly overbased product, for example, 13–14% calcium, or over a range of about 5–14%. Larger amounts can be utilized to form more basic compounds, and the amount of metal base included may be any amount up to that amount which is no longer effective to increase the proportion of metal in the product. When preparing the mixture, the amount of phenol and alcohol included in the mixture is not critical except that the ratio of equivalents of monocarboxylic acid to other components should be at least about 1.1:1; that is, the monocarboxylic acid is present in excess. The ratio of equivalents of the metal base of the combination of the other components in mixture should be greater than 1:1 in order to provide a basic product. More generally, the ratio of equivalents will be at least 3:1.

The step of the process (B) involves treating the mixtures described above with an acidic gas in the absence of free oxygen until the titratable basicity is determined using a phenolphthalein. Generally, the titratable basicity is reduced to a base number below about 10. The first two steps of the process of the present invention require low temperature operating conditions and preferably the exclusion of free oxygen. The ingredients in step (A) are mixed, heated to a low temperature of about 15° C. to about 80° C., and then treated with the acidic gas. After carbonation, and the mixture may be heated to a temperature of about 120–125° C. which is sufficient to drive off water and alcohol contained in the mixture. The treatment of the mixture with the acidic gas preferably is conducted at low temperatures, and the range of temperatures used for this step may be any temperature above ambient temperature up to about 150° C., and more preferably from a temperature of about 15° C. to about 80° C. By the term "acidic gas" as used in this specification and in the claims is meant a gas which upon reaction with water will produce an acid. Thus, such gases as sulfur dioxide, sulfur trioxide, carbon dioxide, carbon disulfide, hydrogen sulfide, etc., are exemplary of the acidic gases which are useful in the process of this invention. Of these acids, sulfur dioxide and carbon dioxide are preferred, and the most preferred is carbon dioxide.

C. Metal Carboxylates or Soaps

The metal carboxylates or soaps are well known primary stabilizers and are preferably selected from the group of zinc, cadmium and tin carboxylates. Metal salts of carboxylic acids having at least six carbon atoms have been widely used as stabilizers for polyvinyl chloride and other halogen-containing polymers. These chemical stabilizers protect halogenated vinyl polymers from rapid decomposition due to exposure to heat and act as hydrochloric acid acceptors. Examples of mono-carboxylic acids used to form these metal soaps include saturated and unsaturated acids, namely, dodecanoic acid, oleic acid, stearic acid, linoleic acid, tall oil acid, or mixtures of one or more of these acids. These carboxylic acids contain from about six to about twenty-two carbon atoms, or more, and an extensive discussion is found in Kirk-Othmer "Encyclopedia of Chemical Technology", 3rd Edition, 1978, John Wiley & Sons, New York, pages 814–871, which is incorporated herein in its entirety by reference.

D. Organic Phosphites

The third step in the process of the present invention involves (C) treating the reaction mixture with at least one organic phosphite which is capable of reducing, inhibiting, and/or eliminating the color-producing component of phenol or phenolic reaction during the above-described process in steps (A) and (B).

Preferably, the composition or reaction product obtained in step (B) is post-treated with at least one organic phosphite. Without limitation, the organic phosphites may be generally characterized by the formula

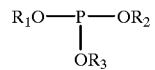

in which $R_1$, $R_2$ and $R_3$ are hydrogen, alkyl, alkenyl, aryl, alkaryl, aralkyl and cycloalkyl radicals or groups, and substituted derivatives thereof. Thus, triphosphites and diphosphites are suitable including trialkyl or dialkyl phosphites, for example, having from about 1 to 18 carbon atoms. Specific examples of organic phosphites, including the preferred liquid organic phosphites, are tributyl phosphite, triisooctyl phosphite and triisodecyl phosphite, diisooctyl phosphite, dibutyl phosphite and tetrakis isodecyl 4,4-isopropylidene diphosphite, diphenyl isodecyl phosphite, phenyl neopentylene glycol phosphite, diphenyl phosphite, triphenyl phosphite, phenyl diisodecyl phosphite and poly (dipropyleneglycol phenyl phosphite. Other organic phosphites may be used in view of this description and exemplification. The amounts of the organic phosphites suitable for use in the treatment are sufficient to inhibit or destroy the color-producing body. More specifically, a molar ratio of phenol to organic phosphite should be between about 0.5–2:1 in order to substantially completely inhibit or destroy the color-producing body.

E. Halogen-Containing Polymer

A halogen-containing polymer, such as a vinyl halide resin, most commonly stabilized with the basic metal salts of this invention is polyvinyl chloride. It is to be understood, however, that this invention is not limited to a particular vinyl halide resin such as polyvinyl chloride or its copolymers. Other halogen-containing resins which are employed and which illustrate the principles of this invention include chlorinated polyethylene, chlorosulfonated polyethylene, chlorinated polyvinyl chloride, and other vinyl halide resin types. Vinyl halide resin, as understood herein, and as appreciated in the art, is a common term and is adopted to define those resins or polymers usually derived by polymerization or copolymerization of vinyl monomers including vinyl chloride with or without other comonomers such as ethylene, propylene, vinyl acetate, vinyl ethers, vinylidene chloride, methacrylate, acrylates, styrene, etc. A simple case is the conversion of vinyl chloride $H_2C=CHCl$ to polyvinyl chloride $(CH_2CHCl-)_n$ wherein the halogen is bonded to the carbon atoms of the carbon chain of the polymer. Other examples of such vinyl halide resins would include vinylidene chloride polymers, vinyl chloride-vinyl ester copolymers, vinyl chloride-vinyl ether copolymers, vinyl chloride-vinylidene copolymers, vinyl chloride-propylene copolymers, chlorinated polyethylene, and the like. Of course, the vinyl halide commonly used in the industry is the chloride, although others such as bromide and fluoride may be used. Examples of the latter polymers include polyvinyl bromide, polyvinyl fluoride, and copolymers thereof.

Mixed metallic carboxylates of liquid overbased calcium carboxylate/carbonate and zinc carboxylate blends with other stabilizers such as beta-diketones, phosphite and phenolic antioxidants have been employed in the following examples to illustrate the practice of this invention. The following examples illustrate the preparation of the basic calcium carboxylate/carbonate salts in accordance with the method of the present invention, but these examples are not considered to be limiting the scope of this invention. Unless otherwise indicated in the following examples and elsewhere in the specification and claims, all parts and percentages are by weight, and all temperatures are in degrees centigrade.

PREPARATION OF STABLE LIQUID OVERBASED CALCIUM CARBOXYLATE

Example 1

Charge mineral oil (290 gm), oleic acid (186 gm), butanol (64 gm), methanol (64 gm), amyl alcohol (64 gm), dodecyl phenol (70 gm), water (19 gm) and calcium hydroxide (243 gm). Start mixing and make sure that all calcium hydroxide is mixed and does not clump up or stick to the bottom of the reactor. Start carbon dioxide sparge, set the flow meter at 3 SCFH. Set the temperature to 40° C., watch the reaction closely, take sample every 0.5 hour and centrifuge. After the carbonation is complete, heat the creation to 120–125° C. over a period of 1 hour. Remove all the distillates from the reaction. Once all the water has been removed, filter the product. The resulting filtered product is a pale brown viscous product containing 13–14% calcium.

Example 2

Charge mineral oil (290 gm), oleic acid (186 gm), butanol (64 gm), methanol (64 gm), amyl alcohol (64 gm), nonyl phenol (60 gm), water (19 gm) and calcium hydroxide (243 gm). Start mixing and make sure that all calcium hydroxide is mixed and does not clump up or stick to the bottom of the reactor. Start carbon dioxide sparge, set the flow meter at 3 SCFH. Set the temperature to 40° C., watch the reaction closely, take sample every 0.5 hour and centrifuge. After the carbonation is complete, heat the reaction to 120–125° C. over a period of 1 hour. Remove all the distillates from the reaction. Once all the water has been removed, filter the product. The resulting filtered product is a pale brown viscous product containing 13–14% calcium.

SHELF STABILITY TESTS

Shelf Stability of the Liquid Overbased Calcium Carboxylate/Carbonate of Example 1 (referred to as New Calcium)

Shelf stability of the liquid overbased calcium carboxylate/carbonate of Example 1 (referred to hereinafter as New Calcium) was measured using a turbidity meter over a two-week period in order to study its shelf stability properties. The Old Calcium referred to hereinafter is a commercially available overbased calcium carboxylate containing 14% Ca (Lubrizol's product, Plastistab 2118).

TABLE I

| | 1 Day | 2 Days | 7 Days | 9 Days | 14 Days |
|---|---|---|---|---|---|
| Stabilizer containing New Calcium | 5.5 | 5.2 | 5.1 | 4.9 | 4.4 |
| Stabilizer containing Old Calcium | >200 | >200 | >200 | >200 | >200 |

Turbidity readings were measured in JTU. The turbidity observation between 1–30 indicates that the product is free from haze, and the observation above 200 JTU indicates that the product is hazy in nature. If the turbidity observation stays constant over a period of time, this means that the product possesses good shelf stability. This means that the product does not pick up any haze or undergo change in physical appearance over a period of time.

The data of Table I shows that the New Calcium possessed good shelf stability over a 2-week period, whereas the commercially available Old Calcium is hazy in nature.

Shelf Stability of Mixed Metal Stabilizer of Overbased Calcium Carboxylate/Carbonate and Zinc Carboxylate (Calcium/Zinc Stabilizer)

Shelf stability of mixed metal calcium/zinc stabilizers containing New Calcium (Example 1) and Old Calcium was also monitored over a period of two weeks as shown in Table II. The stabilizer formulation contained 5% Ca, 1.2% Zn (zinc octoate), 3.5% P (diphenyl isodecyl phosphite), 5% carboxylic acid (oleic acid), 3% anti-oxidant, 3% β-diketone (dibenzoyl methane) and diluent.

TABLE II

| | 1 Day | 4 Days | 8 Days | 14 Days | 17 Days | 21 Days |
|---|---|---|---|---|---|---|
| Stabilizer containing New Calcium | 24.5 | 27.5 | 28.0 | 28.0 | 28.0 | 26.5 |
| Stabilizer containing Old Calcium | >200 | >200 | >200 | >200 | >200 | >200 |

The data illustrates that the incorporation of New Calcium, versus Old Calcium, makes the mixed metal stabilizer shelf stable.

The above shelf stability tests were repeated except New Calcium is a sample of the overbased calcium carboxylate (Example 2) containing 13–14% calcium. Shelf stability of a calcium/zinc stabilizer containing New and Old Calcium was monitored over a period of two weeks and the results are shown in Table III. Stabilizer formulation contained 5% Ca, 1.2% Zn (zinc octoate), 3.4% P (diphenyl decyl phosphite) 6% carboxylic acid (3% oleic acid/3% benzoic acid), 3% nonyl phenol as an anti-oxidant, 2% β-diketone (octyl benzoyl methane) and diluent.

TABLE III

| | 1 Day | 2 Days | 5 Days | 7 Days | 12 Days | 14 Days |
|---|---|---|---|---|---|---|
| Stabilizer containing New Calcium | 26 | 31 | 30 | 28 | 26 | 21 |
| Stabilizer containing Old Calcium | >200 | >200 | >200 | >200 | >200 | >200 |

Again, the data illustrates that the New Calcium produces a shelf stable mixed metal stabilizer versus the Old Calcium.

Shelf Stability of Mixed Metal Overbased Calcium/Cadmium Carboxylate Stabilizers (Calcium/Cadmium Stabilizer)

Shelf stability of a calcium/cadmium stabilizer containing New Calcium (Example 1) and Old Calcium was also monitored over a period of two weeks as shown in Table IV. Stabilizer formation contained 5% Ca, 1.5% Cd (cadmium octoate), 3% P (diphenyl decyl phosphite), 5% carboxylic acid (oleic acid), 2% anti-oxidant (bisphenol-A), 3% β-diketone (dibenzoyl methane) and diluent.

TABLE IV

|  | 0 Days | 1 Day | 3 Days | 4 Days | 7 Days | 14 Days |
|---|---|---|---|---|---|---|
| Stabilizer containing New Calcium | 17 | 29 | 23 | 19 | 16 | 16 |
| Stabilizer containing Old Calcium | >200 | >200 | >200 | >200 | >200 | >200 |

The data illustrates that the incorporation of New Calcium, versus Old Calcium, makes the stabilizer shelf stable.

Shelf Stability of Mixed Metal Overbased Calcium/ Tin Carboxylate Stabilizers (Calcium/Tin Stabilizer)

Shelf stability of a calcium/tin stabilizer containing New Calcium (Example 1) and Old Calcium was also monitored over a period of two weeks as shown in Table V. Stabilizer formulation contained 5% Ca, 1.5% Sn (tin maleate), 3% P (diphenyl decyl phosphite), 5% carboxylic acid (oleic acid), 2% anti-oxidant (bisphenol-A), 3% β-diketone (dibenzoyl methane) and diluent.

TABLE V

|  | 0 Days | 1 Day | 3 Days | 4 Days | 7 Days | 14 Days |
|---|---|---|---|---|---|---|
| Stabilizer containing New Calcium | 34 | 61 | 69 | 76 | 70 | 70 |
| Stabilizer containing Old Calcium | >200 | >200 | >200 | >200 | >200 | >200 |

The data illustrates that the incorporation of New Calcium, versus Old Calcium, makes the stabilizer shelf stable.

Performance Comparisons: Thermal Degradation of PVC

The New Calcium (Example 1) and Old Calcium were incorporated into mixed metal stabilizer compositions for the purpose of observing their relative rate of thermal degradation. The stabilizer compositions are as follows:

|  | A | B |
|---|---|---|
| New Calcium | 5.5% Ca | — |
| Old Calcium (Plastistab 2118) | — | 5.5% Ca |
| Zinc carboxylate | 1.2% Zn | 1.2% Zn |
| Organic Phosphite | 3.0% P | 3.0% P |
| Carboxylic Acid | 4.0% | 4.0% |
| Anti-oxidant | 3.0% | 3.0% |
| Beta Diketone | 3.0% | 3.0% |
| Diluent | as needed | as needed |

The performances of these stabilizers A and B were observed in a PVC formulation containing 100 parts of PVC resin, 30 parts phthalate plasticizer, 3 parts of epoxidized soybean oil and 2 parts of either stabilizer A or B.

Stabilized PVC compounds were then milled at 350–360° F. for 5 minutes at 25 mil thickness. The thermal stability was carried out at 375° F. over 56 minutes. Yellowness [+b chromaticity of CIELAB color space (Commission Internationale de l'Eclairage) developed in 1976] was measured with a Minolta calorimeter. The values of the rate of thermal degradation are shown in the following Table VI.

The PVC formulation containing the stabilizer with the New Calcium (A) develops color at a slower rate than the PVC formulation using the stabilizer with the Old Calcium (B).

TABLE VI

| Time (minutes) | New Calcium A | Old Calcium B |
|---|---|---|
| 7 | 10.51 | 10.3 |
| 14 | 11.28 | 11.35 |
| 21 | 12.57 | 12.51 |
| 28 | 16.29 | 16.1 |
| 35 | 19.5 | 27.6 |
| 42 | 38.26 | 52.83 |
| 49 | 44.77 | 61.28 |
| 56 | 63.97 | 69.38 |

Performance Comparisons: Clarity

The New Calcium (Example 1) and Old Calcium were incorporated into mixed metal stabilizer compositions for the purpose of observing their influence on the clarity of the PVC application. The stabilizer compositions are as follows:

|  | A | B | C |
|---|---|---|---|
| New Calcium | 5.0% | — | — |
| Old Calcium (Plastistab 2118) | — | 5.0% | — |
| Non-Carbonated Calcium Carboxylate | — | — | 5.0% |
| Zinc carboxylate | 1.2% Zn | 1.2% Zn | 1.2% Zn |
| Organic Phosphite | 3.4% P | 3.4% P | 3.4% P |
| Carboxylic Acid | 5.0% | 5.0% | 5.0% |
| Anti-oxidant | 3.0% | 3.0% | 3.0% |
| Beta Diketone | 2.0% | 2.0% | 2.0% |
| Diluent | as needed | as needed | as needed |

The relative degree of clarity of the 0.25 inch pressed PVC formulations containing either stabilizer A, B or C was observed after minutes of exposure to 350° F. and 15,000 pounds pressure. The PVC formulation comprised of 100 parts PVC resin, 30 parts phthalate plasticizer, 3 parts of epoxidized soybean oil and 2 parts of either stabilizer A, B or C.

The pressed PVC samples were placed vertically near printed material to determine the crispness of the print when looking through the press. Stabilizer A and B gave comparable crispness. However, both stabilizer A and B gave better clarity or crispness than stabilizer C.

Performance Comparisons: Plate Out

The New Calcium (Example 1) and Old Calcium along with a non-carbonated calcium carboxylate were incorporated into mixed metal stabilizer compositions for the purpose of observing their influence on the resistance to plate out of the stabilizer during processing of the vinyl formulation. The stabilizer compositions have been identified above as A, B and C with A containing the New Calcium, B containing the Old Calcium and C containing the non-carbonated calcium carboxylate.

Plate out is determined by introducing a red pigment into a PVC formulation containing the stabilizer and allowing the pigment to migrate from the formulation to the metal rolls of a two roll mill at 340° F. A white clean up compound is then placed onto the rolls and the degree of plate out is determined by the amount of red picked up by the clean up compound. The calorimeter assigns a numerical value on the CIElab scale for the degree of redness or plate out (+a).

| Red pigmented formulation: | Clean Up Compound |
|---|---|
| 100 PVC resin | 100 PVC resin |
| 40 phthalate plasticizer | 40 phthalate plasticizer |
| 8 epoxidized soybean oil | 8 epoxidized soybean oil |
| 0.2 stearic acid | 0.2 stearic acid |
| 2 red 2B pigment | 4 Titanium dioxide |
| 1.5 stabilizer variable | 3 lead phosphite |

The red formulation is milled for 4 minutes undisturbed after which the clean up compound is introduced and milled for three minutes undisturbed.

Colorimeter readings, +a value indicating increasing degree of red:

A−3.34
B−3.64
C+21.0

There is essentially no difference between the New and Old Calcium as far as plate out resistance. However, there is a significant difference between A and C where the New Calcium provides superior plate out resistance.

The above description provides a disclosure of particular embodiments of the invention and is not intended for the purpose of limiting the same thereto. As such, the invention is not limited to only the above described embodiments, rather, it is recognized that one skilled in the art would understand alternative embodiments in view of the above description that fall within the scope of the invention.

What is claimed is:

1. A halogen-containing polymer composition comprising a halogen-containing polymer and a heat stabilizing amount of a shelf stable haze free liquid of an overbased calcium oleate prepared by reacting a calcium base with oleic acid and carbonating in the presence of a promoter mixture of a phenol and an alcohol at a temperature up to about 80° C. to produce the shelf stable liquid.

2. A halogen-containing polymer composition of claim 1 wherein the shelf stable liquid has been treated with an organic phosphite in an amount to improve its color.

3. A halogen-containing polymer composition of claim 2 wherein said organic phosphite is a trialkyl phosphite.

4. A halogen-containing polymer composition of claim 3 wherein said phosphite has an alkyl group having from 1 to 18 carbon atoms.

5. A halogen-containing polymer composition of claim 4 wherein said phosphite is selected from the group consisting of tributyl phosphite, triisooctyl phosphite and triisodecyl phosphite.

6. A halogen-containing polymer composition of claim 2 wherein said phosphite is selected from the group of a diphenyl isodecyl phosphite, phenyl neopentylene glycol phosphite, diphenyl phosphite, triphenyl phosphite, phenyl diisodecyl phosphite and poly(dipropyleneglycol) phenyl phosphite.

7. A halogen-containing polymer composition comprising a halogen-containing polymer and a heat stabilizing amount of a shelf stable haze free liquid of an overbased calcium oleate containing at least about 14% calcium prepared by reacting a calcium base with oleic acid and carbonating in the presence of a promoter mixture of an alkyl phenol and an alcohol at a temperature up to about 80° C. to produce the shelf stable liquid.

8. A halogen-containing polymer composition of claim 1 wherein said phenol is selected from the group consisting of dodecylphenol and nonylphenol.

9. A halogen-containing polymer composition of claim 1 wherein the shelf stable liquid has been combined with a metal carboxylate selected from the group consisting of zinc, cadmium and tin carboxylate to make a shelf stable mixed metal stabilizer composition.

10. A process for making a shelf stable haze free liquid of an overbased calcium oleate comprising preparing an overbased calcium oleate/carbonate by reacting a calcium base with oleic acid and carbonating in the presence of a promoter mixture of a phenol and an alcohol, conducting the reaction under a controlled temperature up to about 80° C. to produce a shelf stable haze free liquid.

11. The process of claim 10 which comprises the further step of treating the overbased calcium oleate/carbonate with an organic phosphite in an amount to improve its color.

12. The process of claim 11 wherein said organic phosphite is a trialkyl phosphite.

13. The process of claim 12 wherein said phosphite has an alkyl group having from 1 to 18 carbon atoms.

14. The process of claim 12 wherein said phosphite is selected from the group consisting of tributyl phosphite, triisooctyl phosphite and triisodecyl phosphite.

15. The process of claim 11 wherein said phosphite is selected from the group of a diphenyl isodecyl phosphite, phenyl neopentylene glycol phosphite, diphenyl phosphite, triphenyl phosphite, phenyl diisodecyl phosphite and poly(dipropyleneglycol) phenyl phosphite.

16. The process of claim 10 wherein said calcium base is reacted in an amount to provide about 14% calcium in the overbased calcium oleate.

17. The process of claim 10 wherein said phenol is an alkyl phenol.

18. The process of claim 10 wherein said phenol is selected from the group consisting of dodecylphenol and nonylphenol.

19. The process of claim 10 which comprises the further step of adding a metal carboxylate which is selected from the group consisting of zinc, cadmium and tin carboxylate to make a shelf stable mixed metal stabilizer composition.

20. A shelf stable haze free liquid of overbased calcium oleate produced by the method of claim 10.

21. The liquid of claim 20 containing about 13–14% calcium.

22. The liquid of claim 20 containing about 5–14% calcium.

23. The liquid of claim 20 containing an organic phosphite to improve its color.

24. The liquid of claim 23 wherein said phosphite is selected from the group consisting of tributyl phosphite, triisooctyl phosphite, triisodecyl phosphite, diphenyl isodecyl phosphite, phenyl neopentylene glycol phosphite, diphenyl phosphite, triphenyl phosphite, phenyl diisodecyl phosphite and poly(dipropyleneglycol) phenyl phosphite.

* * * * *